United States Patent [19]

Richardson

[11] Patent Number: 5,003,631
[45] Date of Patent: Apr. 2, 1991

[54] FLIGHT HELMET WITH HEADSET

[75] Inventor: William T. Richardson, Whittier, Calif.

[73] Assignee: Northrop Corporation, Hawthorne, Calif.

[21] Appl. No.: 417,331

[22] Filed: Oct. 5, 1989

[51] Int. Cl.$^5$ .............................................. A42B 3/30
[52] U.S. Cl. .............................................. 2/6; 2/413; 2/423
[58] Field of Search ...................... 2/6, 209, 413, 414, 2/423

[56] References Cited

U.S. PATENT DOCUMENTS

| 2,901,751 | 9/1959 | Gales et al. | 2/6 |
| 2,933,086 | 4/1960 | Gray | 2/209 |
| 3,621,488 | 11/1971 | Gales | 2/6 |
| 3,761,959 | 10/1973 | Dunning | 2/413 |
| 4,700,410 | 10/1987 | Westgate | 2/423 |

FOREIGN PATENT DOCUMENTS 1435878 12/1966 France ................................. 2/423

Primary Examiner—Werner H. Schroeder
Assistant Examiner—Michael A. Neas
Attorney, Agent, or Firm—Terry J. Anderson; Robert B. Block; Karl J. Hoch, Jr.

[57] ABSTRACT

A helmet formed of a rigid shell and, internally thereof, a liner sized and shaped to the head of the wearer with ear cups secured to the liner. The ear cups have a peripheral surface positionable in contact with the wearer's head. The peripheral surface includes a first annular tube filled with a gel material in contact with the wearer's head around the ears and a second annular tube for urging the first annular tube into conforming contact with the wearer's head. The second annular tube is inflatable and includes tubing means extending through the shell with valve means for inflation and deflation thereof. Also disclosed is the method of fabricating the shell to fit an individual wearer.

12 Claims, 3 Drawing Sheets

FLIGHT HELMET WITH HEADSET

BACKGROUND OF THE INVENTION

This invention relates to an improved flight helmet with headset and method of fabrication and, more particularly, to an improved combination helmet and headset which fits more precisely to the individual wearer's head for greater safety, comfort and noise abatement.

DESCRIPTION OF THE BACKGROUND ART

Current flight helmets incorporate standard size ear cups in their headsets. It has been determined that the standard size ear cup does not accommodate the 95th percentile male external ear size. Further, it is not always possible to place the ear cup over the external ear because of the anthropometric differences in the location of the external ears on the heads of the members of the piloting population. In addition, even when properly sized, it has been found that the standard ear cups with a foam rubber seal do not adequately seal the ear against environmental noise.

A wide variety of commercial helmets and headsets are in use today and are disclosed in the patent literature. Typical headsets are disclosed in U.S. Pat. Nos. 2,324,420 and 2,330,730 to Oestrike; 2,619,639 to Hendler; 2,625,683 to Roth; and 2,871,481 to Gerstin. Headsets or earphones are disclosed in U.S. Pat. Nos. 2,801,423 to Shaw; 4,170,275 to Larsen; 4,700,410 to Westgate.

Combinations of helmets and headsets are disclosed in U.S. Pat. Nos. 2,901,751 to Gales; 3,088,002 to Heisig; and 3,621,488 to Gales. Lastly, methods of fabricating helmets or helmets with headsets are disclosed in U.S. Pat. Nos. 3,726,620, 3,882,546, 3,992,721, and 4,044,399 to Morton; 4,239,106 and 4,290,149 to Aileo and 4,432099 to Grick.

As illustrated by a large body of prior art, including the above-noted patents, and a large number of commercial devices, efforts are continuously being made in an attempt to improve helmets, headsets and their methods of fabrication. Nothing in the prior art, however, suggests the present inventive combination of materials and method steps as herein described and claimed. The present invention achieves its purposes, objects and advantages over the prior art through a new, useful and unobvious combination of components and method steps which improve safety, comfort and noise abatement performance.

Therefore, it is an object of this invention to provide a helmet formed of a rigid shell and, internally thereof, a liner sized and shaped to the head of the wearer with ear cups secured to the liner, the ear cups having a peripheral surface positionable in contact with the wearer's head, the peripheral surface including an expandable seal having a first annular tube filled with a gel material in contact with the wearer's head around the ears and a second annular tube for urging the first annular tube into conforming contact with the wearer's head. The second annular tube is inflatable and includes tubing means extending through the shell with valve means for inflation and deflation thereof and bellows formed in the shell for inflation purposes.

It is still a further objection of this invention to size and position headsets in helmets to accommodate the individual needs of the wearer.

It is a further object of the present invention to fabricate helmets with headsets which abate the maximum amount of noise and provide the greatest amount of safety and comfort to the user.

These purposes, objects and advantages should be construed as merely illustrative of some of the more prominent features and applications of the present invention. Many other beneficial results can be obtained by applying the disclosed invention in a different manner or by modifying the invention within the scope of the disclosure. Accordingly, other purposes, objects and advantages as well as a fuller understanding of the invention may be had by referring to the summary herein mentioned and detailed description describing the preferred embodiments of the invention, in addition to the scope of the invention, as defined by the claims, taken in conjunction with the accompanying drawings.

SUMMARY OF THE INVENTION

The present invention is defined by the appended claims with features of the specific embodiments illustrated in the attached figures. For the purposes of summarizing the invention, the invention may be incorporated into a helmet formed of a rigid shell and, internally thereof, a liner sized and shaped to the head of the wearer and ear cups secured to the liner, the ear cups having a peripheral surface positionable in contact with the wearer's head, the peripheral surface including an expandable seal having a first annular tube filled with a gel material in contact with the wearer's head around the ears and a second annular tube for urging the first annular tube into conforming contact with the wearer's head. The second annular tube is inflatable and includes tubing means extending through the shell with valve means for inflation and deflation thereof. Further, bellows are formed in the shell for inflation purposes.

The invention may also be incorporated into a headset comprising a pair of ear cups positionable over the ears of the wearer, the periphery of each earcup being positionable in contact with the wearer's head around his ears, the peripheral surface being formed as an expandable seal including a toroidal tube filled with a gel to conform with the head of the wearer. The expandable seal further includes a pneumatic ring to urge contact between the toroid tube and wearer's head. The pneumatic ring is inflatable and includes tubing means to exterior of the earcup with valve means for inflation and deflation of the pneumatic ring. The tubing means may be a single tube with a one-way valve at the external end thereof. The tubing means may also be a pair of tubes each with a one-way valve at the external end and with a bellows on the end of one of the valves.

Lastly, the invention may be incorporated into a method of fabricating a helmet comprising the steps of (1) providing a shell or rigid material; (2) providing deformable liner material within the shell; (3) positioning a headset, with specifically selected ear cups, to peripherally surround the ears of the particular wearer; (4) heating the shell and liner material (5) positioning the heated shell and liner material over the head of the wearer and the headset; (6) applying pressure from the shell to thereby conform the heated liner to the head of the wearer; and (7) cooling the liner to render it a rigid composite inside the shell. The method further includes the steps of cutting through the liner adjacent to the ear cups to form holes and securing the ear cups to the liner.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the disclosed specific embodiment may be readily utilized as a basis for modifying or designing other helmets and headsets and methods for carrying out the same purposes and objectives of the present invention. It should also be realized by those skilled in the art that such equivalent helmets and headsets and methods do no depart from the spirit and scope of the invention as set forth in the appended claims.

BRIEF DESCRIPTION OF THE DRAWINGS

For a fuller understanding of the nature and objects of the invention, reference should be had to the following detailed description taken in conjunction with the accompanying drawings in which.

Similar reference numerals refer to similar parts throughout the several Figures.

DETAILED DESCRIPTION OF THE INVENTION

Figure 1:
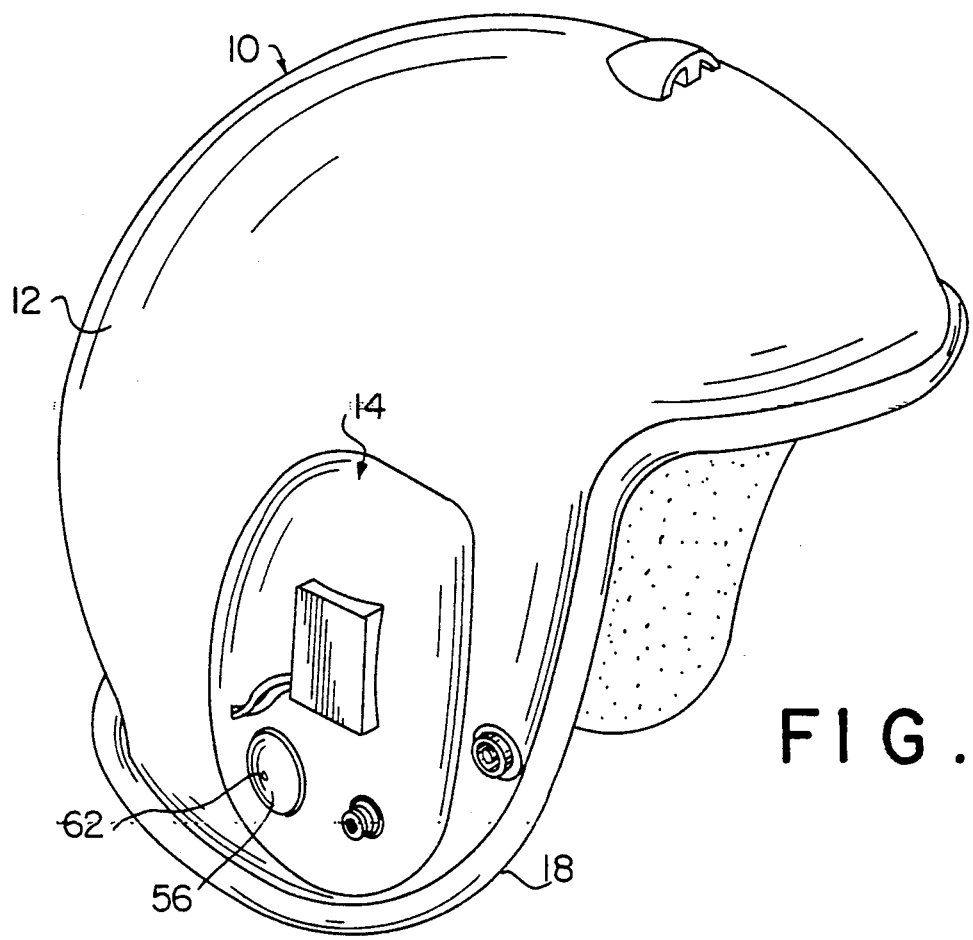
FIG. 1 is a perspective illustration of a helmet with a headset constructed in accordance with the principles of the present invention.
Figure 2:
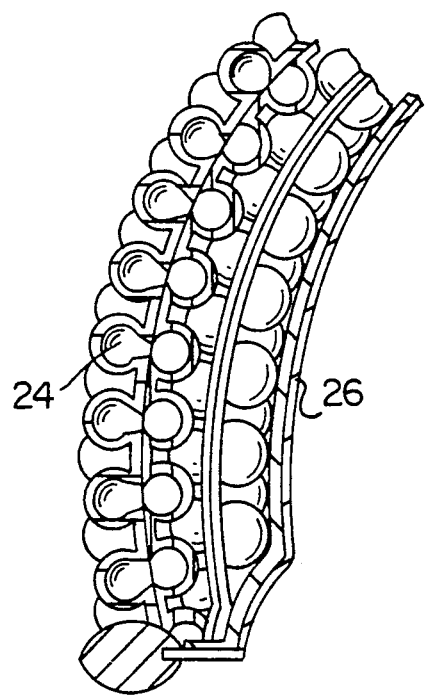
FIG. 2 is an enlarged sectional view of a helmet adjacent to one peripheral edge thereof.
Figure 6:
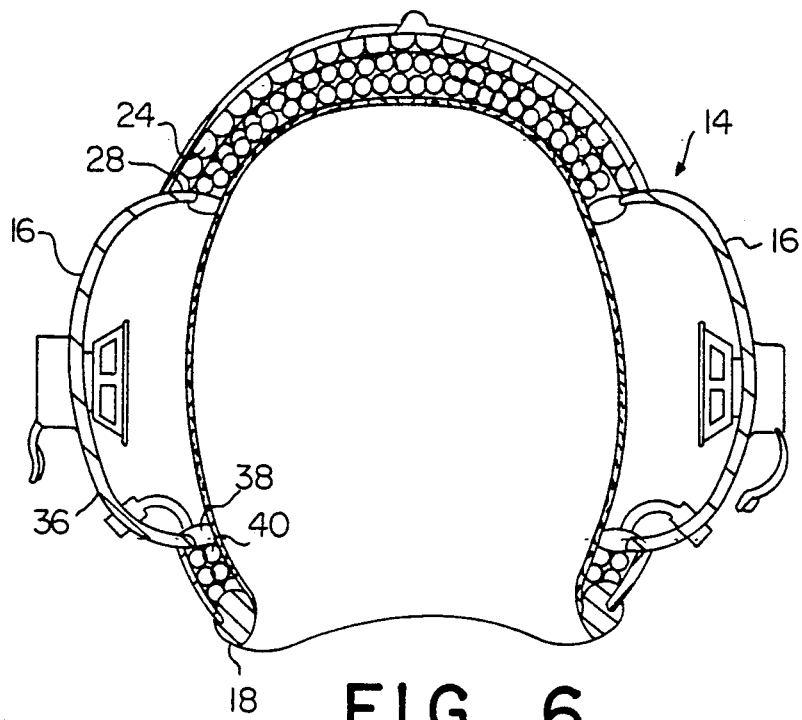
FIG. 6 is a sectional view through an entire helmet with headset similar to FIGS. 1 through 5 but illustrating alternate inflation/deflation mechanisms.
Figure 7:
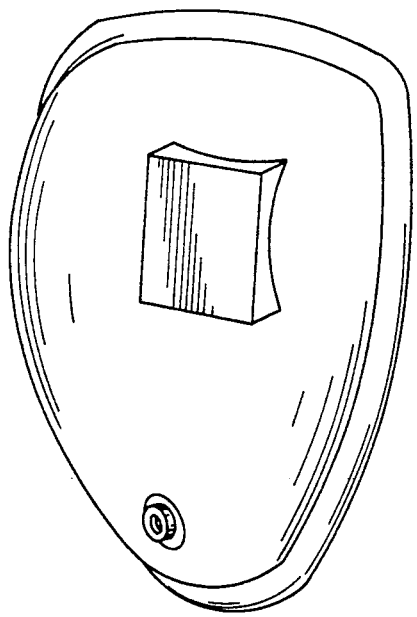
FIG. 7 is a perspective illustration of a portion of a headset similar to FIG. 3 but illustrating the alternate embodiment of the invention shown in FIG. 6.
Figure 8:
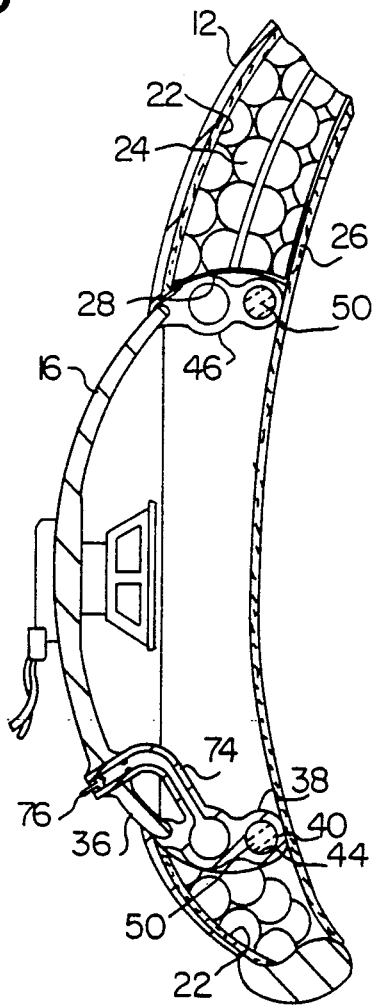
FIG. 8 is a sectional view through a helmet section and ear cup of the embodiment of FIGS. 6 and 7.

Shown in FIG. 1 is a helmet 10 constructed in accordance with the principles of the present invention. The helmet includes a shell 12 and a headset 14. The headset is formed of a pair of ear cups 16. The helmet is formed with the outer shell 12 fabricated of a rigid material and is of a size and shape to cover the skull of a wearer. It has a peripheral edge 18 positioned adjacent the back of the neck of the wearer and extending forwardly beneath the wearer's ears. The shell then extends upwardly along the sides of the wearer's face and across the wearer's forehead. A wide variety of rigid materials may be used for the shell. Commercially available ABS has been found most suitable for its intended purpose of resisting impact and injury during a crash.

Permanently secured to the inner surface of the rigid shell is an inner layer 22 of resilient elastomeric material such as a closed cell polyurethane foam. Secured to the exposed surface of the inner layer is the conformable liner 24 which is shaped to conform to the shape of the head of the individual wearer. Secured to the exposed surface of the conformable liner 24 is an outer layer 26 of cloth to cover the conformable liner. A headset 14 is located in the shell extending through cut out apertures 28 in the conformable liner and shell. The headset is composed of a pair of ear cups 16, one over each ear of a wearer, to complete the helmet. Together, the rigid shell 12, headset 14, and liner 16 are initially of a size to fit a plurality of head sizes.

It has been found that three sizes of helmet shells and headsets are normally sufficient to accommodate most of helmet wearers. In order to accommodate a virtual infinite number of helmet users, the liner 24 is separately formed and subsequently attached t the shell 12 through the resilient inner layer 22.

The liner 24 is formed of one or a plurality of layers of material. The material is a suitable elastic thermoplastic material. A suitable thermoplastic material is ethylene-vinyl-acetate, a copolymer resin available from E. I. duPont deNemours & Company under the trademark "Glvax." The copolymer of ethylene and methacrylic acid is available under the trademark "Surlyin." This latter material is an ionomer resin.

The liner 24 is initially vacuum formed over a hemispherical dome, not shown, with bubbles or protuberances formed at regular intervals across the surface of the dome so that the resulting vacuum formed sheet comprises a hard portion with regularly spaced spherical bubbles. After the layer or layers are vacuum formed, they are trimmed to a required general shape with holes cut out through which the ear cups may pass. The layer or layers are then glued or otherwise secured within the interior of the shell against the inner layer 22. To accommodate a large range of expected head sizes, the liner is formed in a limited number of general sizes using differently sized head forms to determine the size and shape of the different layers during fabrication and assembly.

To custom fit the liner and thus the helmet to the head of the specific individual wearer, the liner is heated to about 200 degrees Fahrenheit for 7 to 10 minutes. After heating, it is promptly placed inside the shell by suitable alignment of coupling fasteners with fasteners carried by the helmet. While still warm, the liner inside the shell is promptly placed on the individual wearer's head and pressed firmly down to conform to the wearer's head until the liner has cooled down, about 3 minutes, or until the liner has cooled to a temperature where it is sufficiently solidified.

After the liner cools to a rigid, non-plastic state, it retains its plastic deformation to provide the desired accommodation over the wearer's head and headset. This procedure may be followed repeatedly to refit the liner either to a different individual or to an individual with a changed head size so long as the new size is at least as large as the previous headsize fitted and in the same size head. The liner readily accommodates changes in head size due, for example, to change in hair length or bumps on the head.

The liner is of such size and configuration to be in conformance with the wearer's head except in the ear areas where it extends around the earcups of the headset. The earphones of the headset may be coupled to the liner permanently by an adhesive or removable as through Velcro or the like. The earcups 16 are preferably fabricated with their shells being with a transparent material such as a polycarbonate so that during fitting, the wearer's ears may be seen for greater accuracy in locating the headset with respect to the wearer's ears.

In accordance with the present invention, the earcups 16 of the headset 14 are also fabricated in a new manner. As is conventional, the exterior 36 of each cup is formed of a rigid material such as polycarbonate. Its interior 38 is a conformable shell having a peripheral surface 40 located in contact with the head of the wearer around the external ear. The periphery 40 of each earcup is fabricated of a pair of hollow rings 44 and 46 coupled together to form an expandable seal portion.

Each first ring 44 which surrounds the ear in contact with the wearer's head is constructed of a continuous hollow member of resilient material filled with a gel 50 of high viscosity, a liquid resistant to flow. In the preferred embodiment, the walls of the ring are fabricated of an elastomeric material having a wall thickness of about between 1 and 2 millimeters. The gel interior thereof has a viscosity of about between 500 and 1,000 centipoise, preferably between 650 and 750 centiposie is preferred. The gel, a silicone fluid, is characterized by its ability to closely conform to the surface adjacent to which it is placed.

Located to the side of the ring 44 of gel material remote from the wearer's head is a second or pneumatic ring 46 adapted to be inflated and deflated to provide a variable force sufficient to urge close conforming contact between the periphery of each earcup and the wearer's head surrounding his external ears. Both rings are formed of a common elastomer such as of a natural or synthetic rubber to effect the inflation of the pneumatic ring 46 and the conforming contact of the gel ring 44 to the wearer's head.

Figure 3:
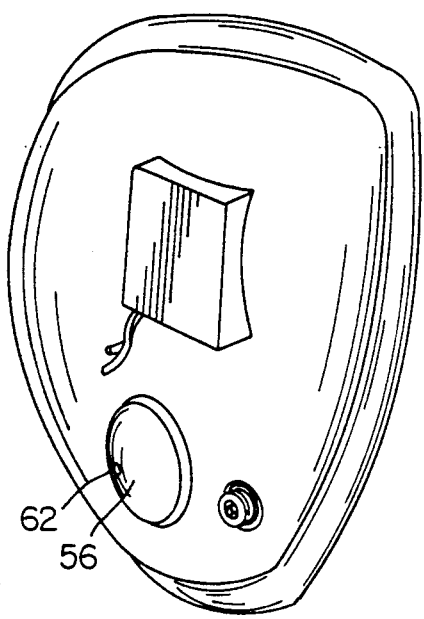
FIG. 3 is an enlarged perspective view of one ear cup of a headset.
Figure 4:
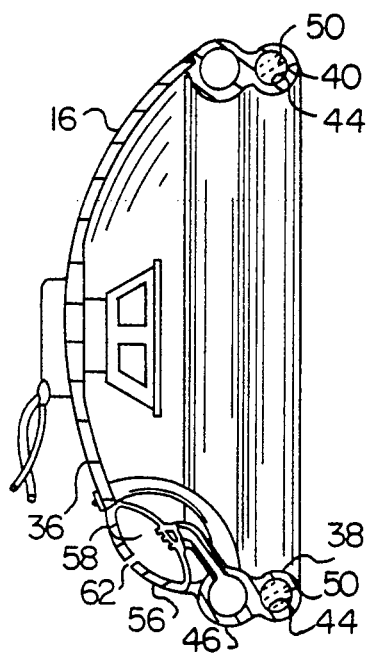
FIG. 4 is an enlarged sectional view through the ear cup shown in FIG. 3.
Figure 5:
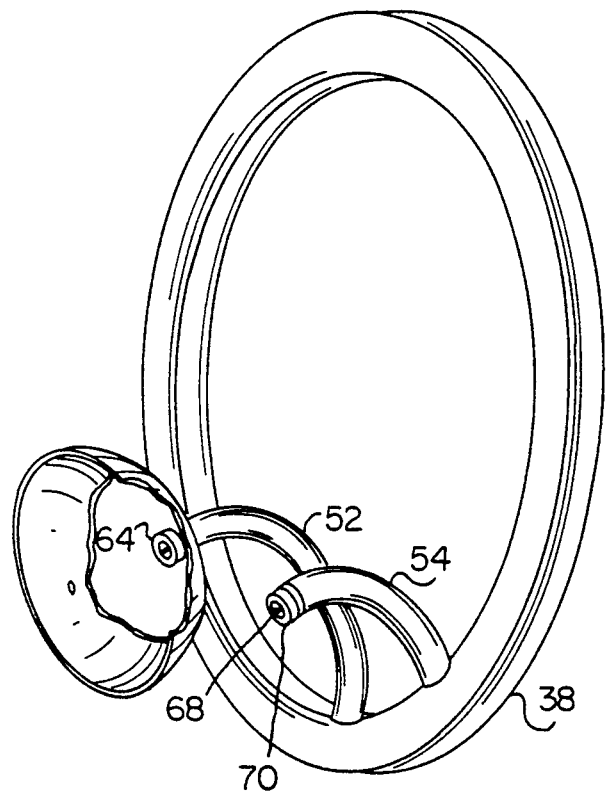
FIG. 5 is an enlarged perspective view of a portion of the periphery of the ear cup shown in FIG. 4 illustrating the inflation and deflation mechanisms.

The pneumatic ring 46 is coupled to the exterior of the headset and helmet through hollow elastomeric tubing 52 and 54. The inflation tubing 52 is coupled at its interior end to the pneumatic ring and has, at its exterior end, a diaphragm 56 for inflation of the pneumatic ring. A chamber 58 is formed in the rigid portion of each earcup. The chamber 58 has an exterior diaphragm 56 of rubber material with a memory to seek the shape as shown in FIGS. 3, 4, and 5. When, however, a wearer positions his or her finger over the aperture 62 in the center of the resilient elastomeric diaphragm and depresses it, the size of the air chamber 58 within the diaphragm is reduced and air is forced to flow through a one-way valve 64 at the exterior end of the inflation tubing. Release of the elastomeric diaphragm will return such member to its shape as shown in FIGS. 3, 4, and 5 to draw additional air through the aperture 62. Once again the wearer may place his or her finger over the aperture and depress the layer to force additional air into the pneumatic ring. By repeating this sequence three, four or more times, additional air may be forced through the one-way valve and retained therein to provide additional pressure against the gel ring to increase its tight conformance with the wearer's head and create an acoustic seal.

Also operatively coupled with the pneumatic ring, is a second tubing 54 for the release of the air from the pneumatic ring. This is done by the operator simply depressing the relief pin 68 of the one-way valve 70 at the outboard end of the second or air release tubing 54. When depressed, the valve 70 will allow the flow of air compressed in the pneumatic ring 46 from the inboard end of the air release tubing 54 through the valve to the atmosphere. With the release of such air, the acoustic seal between the headset of the helmet and the wearer's head is released. Further, under such circumstances, the mechanical coupling between headset and helmet to the wearer's head is reduced to allow removal of the helmet.

In an alternate embodiment of the invention, the tubing pair as shown in FIGS. 4 and 5 is replaced by a single tubing 74 with a single one-way valve 76 at its outboard end. The inboard end of the tubing coupled with the pneumatic ring 46. The pneumatic ring may be inflated by placing a conventional source of compressed air, not shown, at the outboard end of the tubing which will force open a one-way valve 76 at such outboard end. The application of pressurized air to the tubing will thus effect the filling of the pneumatic ring 46. Uncoupling of the compressed air source from the valve 76 will allow the valve to restore to the closed position to retain the air entrapped within the pneumatic ring 46. In order to relieve the pressure adjacent the wearer's head, the wearer merely presses the valve stem extending to exterior of the tubing to reduce the pressure, eliminate the acoustic seal, and allow removal of the helmet.

In fabricating the helmet 10 of the present invention to the individual size of the wearer's head, the headset 14 is selected with earcups 16 of a size to accommodate the individual wearer. The headset is positioned over the wearer's ear with attention paid to the size of the external ears of the wearer as well as their location. Location may be accommodated by positioning the headset earcups in location with an adjustable band of the conventional type extending over the wearer's head. In such position, the periphery of the gel ring 44 is located adjacent to the skull around the external ear of the wearer. The transparency of the earcups assists in precise positioning. The helmet 10 with the bubble pack liner 24 is then positioned over the head of the wearer and around the prepositioned earcups of the headset. The helmet is, however, first heated at about 200 degrees for 7 to 10 minutes with pressure being applied to the lining material by compression between the rigid shell of the helmet and a mold. After being heated, the helmet and liner are placed on the head of the wearer under pressure which will conform the liner to the head of the wearer and around the headset which is located over the wearer's ears. Thereafter the helmet and liner are cooled while still in position over the wearer's head and headset. During cooling, the liner material will be rendered into a rigid composite material beneath the helmet shell. The helmet and liner are then removed with the liner shaped to conform to the wearer's head and the headset. In the preferred embodiment, the liner is cut away in the earcup area with the earcups secured to either the remaining liner and/or the shell. The headset may then be permanently secured in position with respect to the liner and/or the shell as through adhesive, or it may be removably secured as through a pile-type fastener such as Velcro or the like. When in operation and use, the individual helmet has been formed to conform to the individual head of the wearer for greater safety and comfort. In addition, the helmet has been provided with a gel ring and an inflatable pneumatic ring operable for maximizing the conformance of the helmet at the earcup area for superior noise abatement.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details may be resorted to without departing from the spirit and scope of the invention.

Now that the invention has been described,

I claim:

1. A flight helmet with headset custom fit to the head and ears of a particular individual comprising an outer shell of rigid material shaped to cover the head of the wearer and having a peripheral edge lying along the back of the neck and extending forwardly beneath the ears, an inner layer of resilient elastomeric material, a conformable liner of thermoplastic material formed with a generally hemispherical shape, said liner being heated to a temperature at which it can be shaped and inserted into the shell which is then placed on and forced into conformity with the head of the individual for whom it will fit, adhesive means for securing the liner, the layer and the shell together as a unitary structure, means forming left and right ear apertures in the shell, left and right ear cups selected to fully cover the ears of said individual, said ear cups being placed in said apertures, respectively, and positioned while the helmet is worn by said individual so that the ear cups are in a proper sealing position relative to the individual's ear positions, adhesive means for permanently affixing the ear cups to the helmet and liner, an expandable seal surrounding the ear cups so that between the earcup and the head of the wearer a close, noise isolating seal is formed completely around each ear between the head and each earcup.

2. The helmet as in claim 1 in which said ear cups have an expandable seal positionable in contact with the wearer's head, the expandable seal including a first annular tube filled with a gel material in contact with the wearer's head around the ears and a second annular tube for urging the first annular tube into conforming contact with the wearer's head.

3. The helmet as set forth in claim 1 wherein the second annular tube is inflatable.

4. The helmet as set forth in claim 2 wherein the second annular tube includes tubing means extending through the shell with valve means for inflation and deflation thereof.

5. The helmet as set forth in claim 3 and further including bellows formed in the shell for inflation purposes.

6. The headset as in claim 1, wherein a peripheral surface of each ear cup is positioned in contact with the wearer's head around his ears, and is formed as a toroidal tube filled with a gel to conform with the head of the wearer.

7. The headset as set forth in claim 5 and further including a pneumatic ring to urge contact between the toroid tube and the wearer's head.

8. The headset as set forth in claim 6 wherein the pneumatic ring is inflatable.

9. The headset as set forth in claim 7 wherein the pneumatic ring includes tubing means to the exterior of the earcup with valve means for inflation and deflation of the pneumatic ring.

10. The headset as set forth in claim 8 wherein the tubing means is a single tube with a one-way valve at an external end thereof.

11. The headset as set forth in claim 8 wherein the tubing means is a pair of tubes each with a one-way valve at an external end.

12. The headset as set forth in claim 10 and further including a bellows on an end of one of the valves.

* * * * *